United States Patent [19]
Reda

[11] 3,955,252
[45] May 11, 1976

[54] COLLAPSIBLE CORPSE POSITIONER AND RESTRAINER

[76] Inventor: Louis J. Reda, 1645 N. Oak Park Ave., Chicago, Ill. 60635

[22] Filed: Sept. 30, 1974

[21] Appl. No.: 510,394

[52] U.S. Cl. .................................... 27/12; 27/13
[51] Int. Cl.² .................................... A61G 17/00
[58] Field of Search ............... 27/1, 12, 13, 19, 23, 27/25; 248/152, 174; 211/72, 135, 177, 178 R; 15/337, 338

[56] References Cited
UNITED STATES PATENTS

| | | | |
|---|---|---|---|
| 299,665 | 6/1884 | McGrath | 27/13 |
| 377,164 | 1/1888 | Krauser | 27/13 |
| 1,250,937 | 12/1971 | Achert | 248/174 |
| 1,717,272 | 6/1929 | Stanley | 27/13 |
| 1,973,240 | 9/1934 | Werness et al. | 27/13 |
| 3,013,668 | 12/1961 | Mennen | 211/178 R |
| 3,300,166 | 1/1967 | Wojciechowski | 248/174 |
| 3,502,295 | 3/1970 | Sganga | 248/174 |

OTHER PUBLICATIONS

National Wreath & Supply Co., "Cardboard Pillow Positioner," The American Funeral Director, Jan. 1956, p. 60.

*Primary Examiner*—John D. Yasko
*Attorney, Agent, or Firm*—Jerold A. Jacover

[57] ABSTRACT

A corpse positioner and restrainer comprising a substantially rigid member having weakened diagonal portions terminating in a cradling portion is disclosed. The corpse positioner and restrainer further includes cutout portions disposed on opposite sides of said cradling portion, and transverse portions extending from respective cutout portions substantially perpendicularly to opposite edges of the rigid member. The rigid member is adapted to be folded along said weakened diagonal portions until said transverse portions are vertically disposed beneath said cradling portion, whereby said cradling portion is collapsibly supported by said transverse portions.

4 Claims, 5 Drawing Figures

COLLAPSIBLE CORPSE POSITIONER AND RESTRAINER

BACKGROUND OF THE INVENTION

This invention generally relates to a corpse support, and in particular relates to a device used for positioning, supporting and restraining corpse extremities, such as the head, in an upwardly stable position inside a casket.

There are many circumstances in which a human corpse is dressed and prepared for burial in one location, and delivered in a casket to a funeral parlor, or other similar place, for viewing by mourners prior to burial. During transit it is essential that the corpse extremities, particularly the head, be maintained in an upwardly stable position. If the head is not so maintained, an undesirable outflow of bodily liquids and embalming fluids may result, thereby marring the body and permanently staining the casket interior, thus rendering the corpse unfit for viewing upon arrival at its destination.

In the past, some attempts have been made to alleviate the problem hereinbefore described. One such attempt involved the use of an undertaker's block having at least one concave surface. This surface was conventionally slipped under the nape of the deceased's neck, thereby maintaining the head in such a position as to preclude the outflow of bodily liquids or embalming fluids. Though these undertaker's blocks have been successfully employed, their relatively large size posed storage problems for undertakers who had to keep numerous blocks on hand for immediate use. Moreover, the undertaker's blocks of the prior art were generally fabricated from wood, rubber, or the like, and were therefore both heavy and expensive.

Accordingly, it is a primary object of this invention to provide an improved corpse positioner and restrainer.

It is another object of this invention to provide an improved corpse positioner and restrainer which requires minimal storage space.

It is a further object of this invention to provide an improved corpse positioner and restrainer which is both lightweight and inexpensive.

The corpse positioner and restrainer of the invention achieves these and other objects in a novel yet uncomplicated structure. More particularly, the corpse positioner and restrainer comprises a member which can be stored in a minimal amount of space. The member may be fabricated from pasteboard, or similar material, and is therefore relatively lightweight and inexpensive. Moreover, the structure is assembled with minimal effort and skill, and when in use provides reliably strong support for corpse extremities such as the head.

SUMMARY OF THE INVENTION

The corpse positioner and restrainer of the invention comprises a substantially rigid member having weakened diagonal portions terminating in a cradling portion. The corpse support further comprises cutout portions disposed on opposite sides of the cradling portion, and transverse portions extending from respective cutout portions substantially perpendicularly to opposite edges of the rigid member. The rigid member is adapted to be folded along the weakened diagonal portions until the transverse portions are vertically disposed beneath the cradling portion, whereby the cradling portion is collapsibly supported by the transverse portions.

BRIEF DESCRIPTION OF THE DRAWINGS

The corpse positioner and restrainer of the invention can best be understood by reading the following detailed description in conjunction with the accompanying drawings in which.

DETAILED DESCRIPTION OF AN EXEMPLARY EMBODIMENT

Figure 1:
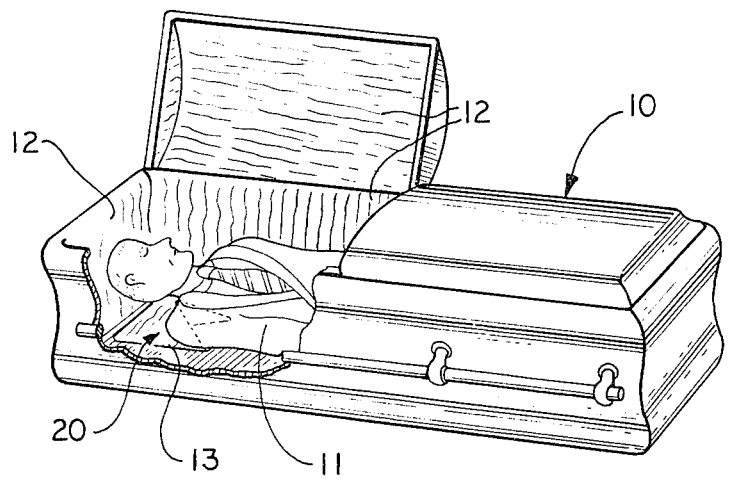
FIG. 1 is a perspective view of a casket illustrating the corpse positioner and restrainer of the invention in use to support the head of a deceased.

Referring now to FIG. 1, there is shown a casket 10 carrying a prepared corpse 11. During preparation, the corpse is dressed pursuant to conventional undertaking practices, and the interior of casket 10 is customarily draped with fancy material 12 such as silk, satin, or plush velvet. Such preparation creates an aura of beauty and dignity for mourners who may subsequently wish to view the deceased prior to burial.

A corpse positioner and restrainer 20 is disposed under the nape of the deceased's neck, thereby maintaining the head of the deceased in an upwardly stable position. Thus, the head of the deceased will not tip sidewise or downward if the casket is jostled during transit from the point of preparation to the place of viewing by mourners. Accordingly, abdominal liquids and embalming fluids contained within corpse 11 cannot spew forth from the mouth or nose, thereby marring the appearance of corpse 11 or material 12. If desired, corpse positioner and restrainer 20 can be covered with material 13, matching material 12. Material 13 can be fastened to corpse positioner and restrainer 20 in any suitable way, such as by staples 14 shown in FIG. 3. For purposes of clarity, however, material 13 is not shown in FIGS. 2, 4, 5.

Figure 2:
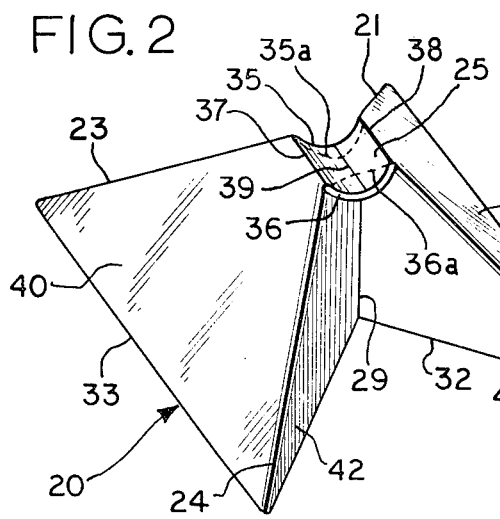
FIG. 2 is an enlarged perspective view of the corpse positioner and restrainer shown in FIG. 1.
Figure 3:
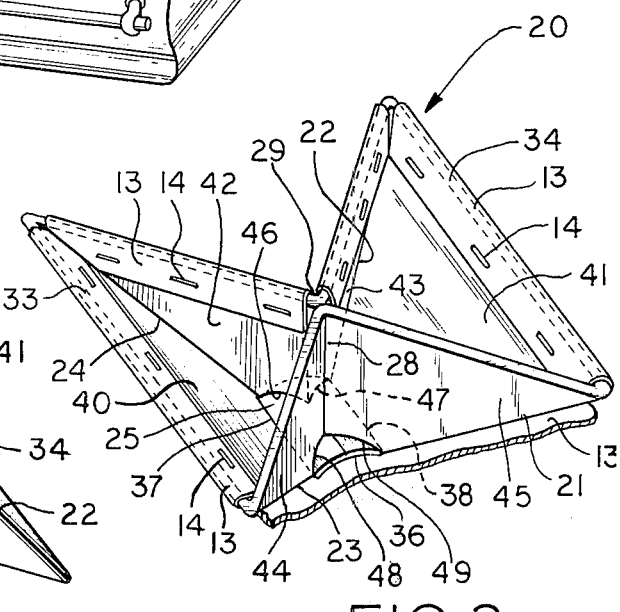
FIG. 3 is a perspective view of the bottom of the corpse positioner and restrainer shown in FIG. 2.
Figure 4:
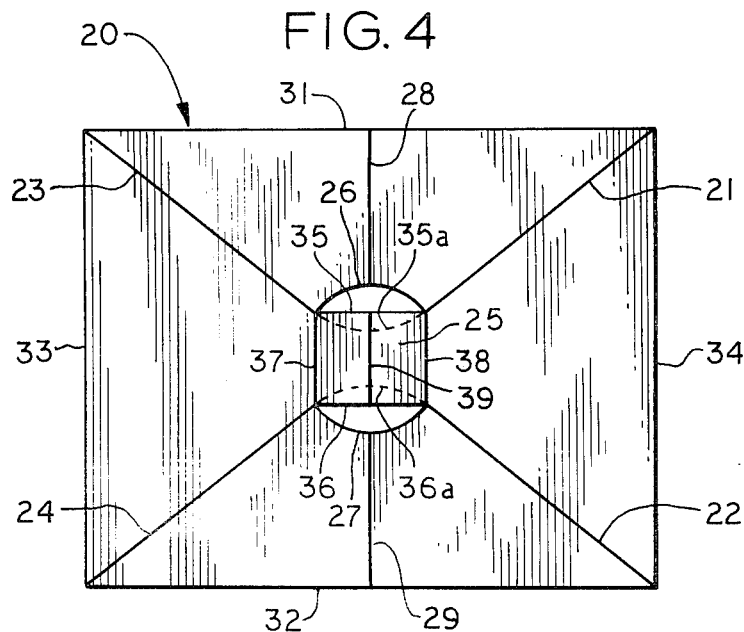
FIG. 4 is a plan view of the corpse positioner and restrainer shown in FIG. 2 in collapsed form.
Figure 5:
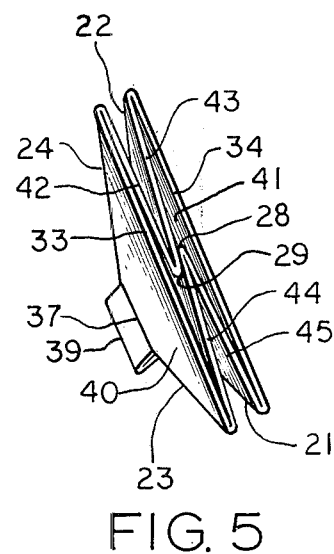
FIG. 5 is a perspective view of the corpse positioner and restrainer shown in FIG. 2 in an alternative collapsed form.

A preferred embodiment of corpse positioner and restrainer 20 is shown more clearly in assembled form in FIGS. 2–3, and in collapsed form in FIGS. 4–5. When in the collapsed form of FIG. 4, the corpse positioner and restrainer 20 lies substantially flat, enabling several such supports to be stored in a minimal amount of space prior to use by stacking them on top of each other. More particularly, as shown in FIG. 4, one collapsed form of corpse positioner and restrainer 20 has a substantially rectangular shape defined by parallel, lengthwise edges 31, 32 and parallel, widthwise edges 33, 34. In the preferred embodiment, lengthwise edges 31, 32 are 31 inches long and widthwise edges 33, 34 are 22¾ inches long. Of course, these and any other preferred dimensions set forth herein should be construed as limitative, the scope of the invention being defined in the appended claims.

The corpse positioner and restrainer shown in FIG. 4 is preferably fabricated from pasteboard having a corrugated inner layer sandwiched between a pair of multi-ply outer layers. Weakened diagonal portions 21, 22, 23, 24, extending from each corner of the rectangular-shaped corpse positioner and restrainer toward the center thereof, are made in any suitable way such as by folding, creasing perforating or partially slitting corpse positioner and restrainer 20. In the preferred embodiment, weakened diagonal portions 21, 22, 23, 24 are made by cutting through one outer layer and the corrugated inner layer, leaving the other outer layer intact.

In one aspect of the preferred embodiment, diagonal portions 21, 22, 23, 24 terminate at the corners of a rectangular cradling portion 25, disposed in the center of corpse positioner and restrainer 20, and defined by parallel lengthwise edges 35, 36 and parallel widthwise edges 37, 38. In this aspect of the preferred embodiment. lengthwise edges 35, 36 are 10 inches long and widthwise edges 37, 38 are approximately 1-$\chi$ inches long. Disposed along each of lengthwise edges 35, 36 are corresponding cutouts 26, 27. Cutouts 26, 27 are preferably semicircular-shaped, having a preferred radius of 2-$\chi$ inches, and permit portions of corpse positioner and restrainer 20 to be moved under cradling portion 25 to support the same in a manner described in greater detail hereinafter.

In another aspect of the preferred embodiment, cradling portion 25 is not rectangular, but has concave lengthwise edges 35a and 36a as illustrated by the dashed lines in FIG. 4. For reasons that will become more apparent hereinafter, these concave lengthwise edges 35a and 36a prevent cradling member 25 from overhanging cutouts 26, 27 when corpse positioner and restrainer 20 is assembled.

Corpse positioner and restrainer 20 further includes a pair of transverse portions 28, 29 extending from respective cutouts 26, 27 perpendicularly toward the midpoints of respective lengthwise edges 31, 32. A crease 39, along the same line defined by transverse portions 28, 29 is disposed transversely across cradling portion 25. Thus, when corpse positioner and restrainer 20 is assembled, crease 39 of cradling member 25 rests upon the arcuate edges defined by cutouts 26, 27 and is buttressed by transverse portions 28, 29.

Assembly of corpse positioner and restrainer 20 from the collapsed form of FIG. 4 is achieved by urging transverse portions 28, 29 toward each other. When this is done, the surface of corpse positioner and restrainer 20 gives way along weakened diagonal portions 21, 22, 23, 24. When this occurs, corpse positioner and restrainer 20 is transformed from the flat, collapsed member depicted by FIG. 4 into a polyhedron shown in FIGS. 2 and 3.

In the collapsed form of FIG. 5, corpse positioner and restrainer 20 is folded along diagonal portions 21, 22, 23, 24, with transverse portions 28, 29 internally nestled as shown. Cradling member 25 is bowed about crease 39, thus giving corpse positioner and restrainer 20 a substantially flat, triangular shape. Assembly of corpse positioner and restrainer 20 from the alternate collapsed form of FIG. 5 is achieved by pulling outwardly on widthwise edges 33 and 34, unnestling transverse portions 33, 34 until the polyhedron shown in FIGS. 2 and 3 results.

The polyhedron of FIGS. 2 and 3 is characterized by a pair of oppositely disposed trapezoidal faces 40, 41 and a concave top face heretofore referred to as cradling portion 25. The polyhedron is further characterized by a first pair of right triangular faces 42, 43, disposed between diagonal portions 24 and 22, having arcuately truncated apices 46, 47. Right triangular faces 42, 43 have a common leg heretofore referred to as transverse portion 29. Similarly, a second pair of right triangular faces 44, 45, disposed between diagonal portions 23 and 21, have arcuately truncated apices 48, 49. Right triangular surfaces 45, 46 also have a common leg heretofore referred to as transverse portion 28.

As mentioned hereinbefore, the corpse positioner and restrainer of the invention is assembled from the collapsed form of FIG. 4 by urging transverse portions 28, 29 toward each other, and assembled from the collapsed form of FIG. 4 by unnestling transverse portions 28, 29. When this is done properly, transverse portions 28, 29 will very nearly abut, as shown in FIG. 3, causing right triangular face 42 to form an angle less than 180° with right triangular face 43. Similarly, right triangular face 44 will form an angle less than 180° with right triangular face 45. As shown in FIG. 2, when corpse positioner and restrainer 20 is assembled, cradling portion 25 dips downwardly so that crease 39 rests on arcuately truncated apices 46, 47, 48, 49. If cradling portion 25 is not rectangular, but has concave lengthwise edges 35a and 36a, there will be no overlap of cradling member 25 beyond arcuately truncated apices 46, 47, 48, 49 as defined by cutouts 26, 27. Transverse portions 28, 29 reliably support cradling member 25 in conjunction with faces 40, 41, 42, 43, 44 and 45. When so assembled, corpse positioner and restrainer 20 can then be placed under the nape of the neck of a deceased as illustrated in FIG. 1, thereby assuring that the deceased's head will remain in place.

Though the embodiment of the corpse positioner and restrainer herein described is preferred, it will be apparent to those skilled in the art that numerous refinements, improvements and modifications can be made without departing from the true scope of the invention. Accordingly, all such refinements, improvements and modifications are intended to be covered by the appended claims.

I claim:

1. A corpse positioner and restrainer comprising: a substantially rigid and substantially rectangular member having weakened diagonal portions terminating in a center, cradling portion; said cradling portion adapted to be placed under a predetermined anatomical portion of a corpse for supporting said anatomical portion; means defining cutout portions disposed on opposite sides of said cradling portion; and transverse portions defined by a crease through said cutout portions and through the center of said rectangular member, said crease extending perpendicularly from one side of said rectangular member to the opposite side thereof; said transverse portions being adapted to form vertical supports for said cradling portion upon folding said rectangular member along said weakened diagonal portions and along said crease.

2. The corpse positioner and restrainer recited in claim 1 wherein said cutout portions are semicircularly shaped.

3. The corpse positioner and restrainer recited in claim 1 wherein said rigid member is fabricated from corrugated pasteboard.

4. A corpse positioner and restrainer comprising: a polyhedron having a pair of oppositely-disposed trapezoidal faces; a concave top face connecting said trapezoidal faces; a first pair of right triangular faces having a common leg and truncated apices to accommodate said top concave face, said first pair of right triangular faces being disposed at an angle less than 180° relative to each other, connecting corresponding edges of said oppositely-disposed trapezoidal faces; and a second pair of right triangular faces having a common leg and truncated apices to accommodate said top concave face, said second pair of right triangular faces being disposed at an angle less than 180° relative to each other, connecting other corresponding edges of said oppositely-disposed trapezoidal faces, whereby said concave top face is supported by said pair of oppositely-disposed trapezoidal faces and by said first and second pair of right triangular faces, permitting said concave top face to cradle a corpse head.

* * * * *

UNITED STATES PATENT AND TRADEMARK OFFICE
CERTIFICATE OF CORRECTION

PATENT NO. : 3,955,252
DATED : May 11, 1976
INVENTOR(S) : Louis J. Reda

It is certified that error appears in the above-identified patent and that said Letters Patent are hereby corrected as shown below:

In Column 3, line 16, "1-$x$" should be "1-7/8"

In Column 3, line 20, "2-$x$" should be "2-7/8"

Signed and Sealed this

Thirteenth Day of July 1976

[SEAL]

Attest:

RUTH C. MASON
Attesting Officer

C. MARSHALL DANN
Commissioner of Patents and Trademarks